United States Patent [19]

Kwok et al.

[11] Patent Number: 5,801,292
[45] Date of Patent: Sep. 1, 1998

[54] ALDEHYDE PROCESS

[75] Inventors: Thomas J. Kwok, Flanders, N.J.; Windell C. Watkins, Longview, Tex.

[73] Assignee: Eastman Chemical Company, Kingsport, Tenn.

[21] Appl. No.: 623,072

[22] Filed: Mar. 28, 1996

[51] Int. Cl.⁶ .................................................. C07C 45/45
[52] U.S. Cl. ........................ 568/463; 568/459; 568/464
[58] Field of Search ............................... 568/459, 463, 568/464

[56] References Cited

U.S. PATENT DOCUMENTS

| | | | |
|---|---|---|---|
| 4,263,181 | 4/1981 | Wagner et al. | 260/9 |
| 5,144,089 | 9/1992 | Arena et al. | 568/463 |

FOREIGN PATENT DOCUMENTS

| | | |
|---|---|---|
| 1230558 | 9/1960 | France . |
| 898739 | 10/1953 | Germany . |

OTHER PUBLICATIONS

Tsuji H et al, "Self–Condensation of n–Butyraldehyde over Solid Base Catalysts;" J. Catal.; 1994; vol. 148 (2) ; pp. 759–770.

Zhang G et al, "Aldol Addition of Butyraldehyde over Solid Base Catlaysts"; Bull. Chem. Soc. Japan; 1989; vol. 62 (6); pp. 2070–2072.

Chemical Abstracts, vol. 126, No. 21; Abstract No. 277185d, Ichikawa M et al, 1997.

*Primary Examiner*—Allen J. Robinson
*Assistant Examiner*—Barbara Badio
*Attorney, Agent, or Firm*—Michael J. Blake; J. Frederick Thomsen; Harry J. Gwinnell

[57] ABSTRACT

A process for condensing aldehydes where an aldehyde having an a hydrogen and having the formula $R_1CHO$, wherein $R_1$ is selected from alkyl having one to twelve carbon atoms and aralkyl having one to fourteen carbon atoms, is combined with hydrated MgO to form a reaction product comprising an aldol of said aldehyde, the unsaturated aldehyde derived by dehydration of said aldol, or mixtures thereof. In a second embodiment, a first composition selected from aldehydes containing an a hydrogen and having the formula $R_1CHO$, wherein $R_1$ is as defined above, is combined with a second composition selected from aldehydes having the formula $R_2CHO$, wherein $R_2$ is selected from H, alkyl having one to twelve carbon atoms, and aralkyl having one to fourteen carbon atoms, and with hydrated MgO, to form a reaction product mixture comprising an aldol of said aldehyde, the unsaturated aldehyde derived by dehydration of said aldol, or mixtures thereof. The aldol or aldehyde formed may be separated from the reaction product mixture, and recovered or treated as desired, or the reaction product mixture may be further directly treated, such as by hydrogenation, to produce a desired product admixture.

32 Claims, No Drawings

ALDEHYDE PROCESS

FIELD OF THE INVENTION

The invention relates generally to a process for condensation of aldehydes, and more particularly to a process for forming desired aldols by the reaction of specified aldehydes in the presence of a novel catalytic agent.

BACKGROUND OF THE INVENTION

The reaction of aldehydes in the so-called "aldol condensation" reaction is well known. In this reaction, a nucleophilic ion, produced, for example, by the action of a strong base or alkali on an aldehyde having an α hydrogen atom, adds to the carbonyl group of another aldehyde molecule. The aldehyde-alcohol (aldol) produced by the reaction may be recovered, or it may be treated directly in the reaction system or reaction product admixture to form a desired composition. In many instances, the aldol de-hydrates spontaneously or promptly in the process admixture or environment, or is easily dehydrated, forming an unsaturated aldehyde, which can be recovered or treated further. For example, n-butyraldehyde readily may be condensed and dehydrated to 2-ethyl-2-hexenal according to the following reactions:

(I)

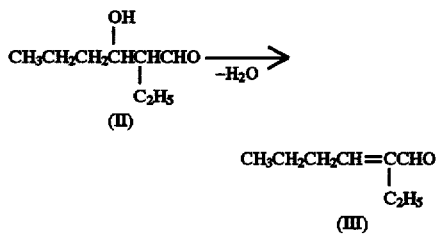

Although the aldol composition enumerated as (II) may be isolated, its dehydration to (III) is, as indicated, usually very easily accomplished under the reaction conditions for the condensation. Accordingly, it is the unsaturated aldehyde (III) which is generally recovered. Hydrogen reduction of (III) gives 2-ethylhexanol, as follows:

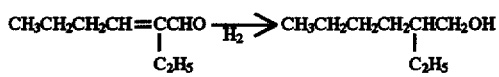

As is also commonly known, the aldol condensation reaction may be used not only for the condensation of a given aldehyde, but for the combination of different aldehydes, producing a so-called "cross aldol", provided that at least one of the aldehydes contains an α hydrogen. For example, isobutyraldehyde may be reacted or condensed with formaldehyde in the presence of alkali, under suitable conditions, to form hydroxypivaldehyde. The hydroxypivaldehyde may, if desired, be hydrogenated to form neopentyl glycol, a valuable commodity chemical.

These reactions are shown, as follows:

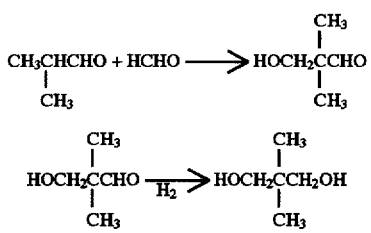

Commonly, strong bases, such as alkali metal hydroxides, are utilized as the catalytic agents in aldol condensation, especially if the reaction is conducted in aqueous solution. The use of alkali metal hydroxides, however, has a number of disadvantages. For example, alkali metal hydroxides present problems because they are highly reactive and because they form salts. In this regard, U.S. Pat. No. 5,144,089 (Arena, et al), dated Sep. 1, 1992, discusses the unsuitability of solid alkali metal hydroxides for certain fixed bed aldehyde condensation processes. To avoid the use of alkali metal hydroxides, these patentees employ solid solutions of magnesium oxide-aluminum oxide, said to be related to hydrotalcite, or what previously has been referred to as synthetic hydrotalcites, in a fixed mass. However, better conversions and selectivity in their procedure appear to require higher temperatures coupled with long residence times, and fixed bed operations are required. Accordingly, there has remained a need for an effective procedure for aldehyde condensation which does not have the disadvantages associated with alkali metal hydroxides or which does not require lengthy residence times or fixed bed operations. The invention addresses this need.

SUMMARY OF THE INVENTION

In one embodiment, therefore, the invention relates to a process for the condensation of an aldehyde comprising contacting or combining aldehyde containing an α hydrogen atom and having the formula $R_1CHO$, wherein $R_1$ is selected from alkyl having one to twelve carbon atoms, and aralkyl having one to fourteen carbon atoms, with a catalytic amount of hydrated MgO (magnesium oxide) under reaction conditions to form reaction product mixture comprising or containing an aldol of said aldehyde, the unsaturated aldehyde derived by dehydration of said aldol, or mixtures thereof. As used herein, the expression "the unsaturated aldehyde derived by dehydration of said aldol" refers to the α, β-olefinic aldehyde resulting from the decomposition of the aldol produced by the condensation, which decomposition also results in or is characterized by the formation of water as a product.

In a second embodiment, the invention relates to an aldehyde condensation process comprising contacting or combining a first aldehyde selected from aldehydes containing an α hydrogen atom and having the formula $R_1CHO$, wherein $R_1$ is selected from alkyl having one to twelve carbon atoms, and aralkyl having one to fourteen carbon atoms, with a second different aldehyde selected from aldehydes having the formula $R_2CHO$, wherein $R_2$ is selected from H, alkyl having one to twelve carbon atoms, and aralkyl having one to fourteen carbon atoms, with a catalytic amount of hydrated MgO, under reaction conditions to form reaction product mixture comprising or containing an aldol of said aldehydes, the unsaturated aldehyde derived by dehydration of said aldol, or mixtures thereof. Accordingly, the reaction product mixtures of the invention will comprise or contain one of (A) the aldol of the aldehyde condensed, or of the aldehydes cross condensed; (B) the unsaturated aldehyde derived by dehydration of said aldol; or (C) a mixture of (A) and (B).

Further according to the invention, any stable aldol formed in either embodiment may be separated from the reaction mixture produced, and treated as desired, e. g., hydrogenated to form a hydrogenated mixture containing a di-alcohol, or reaction product mixture may be treated directly. In the latter case, for example, direct hydrogenation of the reaction mixture will form a hydrogenated admixture containing a di-alcohol therein. Again, if the aldol formed in either embodiment dehydrates under the reaction conditions in the reaction zone, or is readily dehydrated, e. g., by heating, to form an unsaturated aldehyde, the unsaturated aldehyde may be separated and treated, or the reaction product mixture may be treated, such as by directly hydrogenating the mixture, to produce a desired hydrogenated product mixture or admixture.

Preferably, according to the invention, the hydrated MgO is supplied for contact with the aldehyde or aldehydes to be condensed in a manner which provides intimate contact of the catalyst particles with the aldehyde(s). For example, the hydrated MgO may be supplied to the reaction zone as an aqueous slurry of the hydrated particles, the combination of the aldehyde(s) and aqueous slurry, on sufficient agitation, forming a heterogeneous admixture containing suspended hydrated MgO particles. Because water will generally be present, either from aldol dehydration or by purposeful addition thereof, the hydrated character of the MgO will remain intact. An important advantage of the invention is the ability to separate the hydrated MgO from reaction product mixture, e. g., by filtration or other means, to the end that the separated hydrated MgO may be reused by supplying the separated hydrated MgO to the reaction zone for contact with the aldehyde in a continuous procedure, the reused hydrated MgO exhibiting the same or essentially the same catalytic activity as initially. Moreover, problems attendant the use of alkali metal hydroxides, such as salt disposal, are avoided. The invention is particularly useful for the condensation of n-butyraldehyde and the cross condensations of n-butyraldehyde, or isobutyraldehyde, with formaldehyde.

DETAILED DESCRIPTION OF THE INVENTION

As indicated, in the first embodiment of the invention, the composition employed in the reaction process is selected from aldehydes containing an α hydrogen atom and having the formula $R_1CHO$, wherein $R_1$ is selected from alkyl having or containing one to twelve carbon atoms and aralkyl having or containing one to fourteen carbon atoms. The alkyl and aralkyl moieties of the aldehyde may contain or comprise straight chain or branched chain portions, and the position of aryl groups in the aralkyl moiety is not critical. Particularly preferred aldehydes for the condensation are previously mentioned n-butyraldehyde, propionaldehyde, isobutyraldehyde, acetaldehyde, valeraldehyde, and phenylacetaldehyde. In the second or "cross-aldol" embodiment of the invention, the first aldehyde composition is also selected from aldehydes containing an α hydrogen atom and having the formula $R_1CHO$, wherein $R_1$ is selected from alkyl having or containing one to twelve carbon atoms, and aralkyl having or containing one to fourteen carbon atoms, as described, and the preferred aldehydes correspond to those above-mentioned. However, the second aldehyde composition combined therewith or contacting the first aldehyde composition is a different aldehyde selected from aldehydes having the formula $R_2CHO$, wherein $R_2$ is selected from H, alkyl having or containing one to twelve carbon atoms, and aralkyl having or containing one to fourteen carbon atoms. As will be understood by those skilled in the art, the alkyl and aralkyl portions of the aldehyde selected as the second aldehyde may or may not possess an a hydrogen atom. A listing or grouping of aldehydes selected for the second aldehyde composition, however, preferably coincides with that mentioned for the first aldehyde composition with the important exception that formaldehyde may be used.

As will be understood by those skilled in the art, the condensation reaction tends to produce, in many cases, a mixture of aldols in the reaction product mixture. For example, in case of "self" condensation of an aldehyde, uncondensed aldehyde may condense with the aldol formed, since it also is an aldehyde, while in the case of "cross" condensation, it is possible for one of the different uncondensed aldehydes (except formaldehyde) to self condense. The process of the invention, however, produces excellent selectivities in many cases to the desired aldols. For simplicity hereinafter, the expression "aldol of said aldehyde" is taken herein to refer to the first or primary condensation product of the aldehyde employed, while the expression "aldol of said aldehydes" refers to the cross condensation product of the different aldehydes employed as reactants in the second embodiment of the invention. The aldols contemplated, therefore, will contain, in the first embodiment, a number of carbon atoms which is twice that of the aldehyde employed, and, in the second embodiment, will contain a number of carbon atoms which is the sum of the carbon atoms contained in the respective aldehydes; in both cases, the aldol will not contain more than one hydroxyl group. As indicated, in many instances, the aldol formed dehydrates spontaneously in the reaction product mixture, under the reaction conditions, to form an α, β- olefinic aldehyde. Where the aldol has stability, heating the reaction product mixture, e.g., from 70° C. to 200° C., will generally accomplish the dehydration, or the aldol may be separated and then heated in this temperature range to dehydrate. The unsaturated aldehyde may be the desired composition, or, as is commonly the case, is treated, such as by hydrogenation, to form a desired end product.

While it is not a requirement of the invention that the aldehyde or aldehydes chosen in either embodiment be pure or substantially pure, selectivity to the desired aldol may be impaired in the reaction in proportion to the amount of impurity or undesired reactant present. Accordingly, some concentration of other compositions may be present in the aldehyde or aldehydes employed so long as the compositions do not interfere significantly with the condensation reaction or with the desired end use of the products of the invention. The process of the invention may also be used for aldehyde removal from a variety of compositions if desired. As indicated previously, n-butyraldehyde and isobutyraldehyde are important first aldehyde compositions for cross condensation with formaldehyde.

A critical aspect of the invention is the use of hydrated MgO for catalyzing or promoting the condensation reaction. As understood herein, the phrase "hydrated MgO" refers to solid particulate MgO (magnesium oxide) which has been treated or contacted with sufficient water (including wet steam) for a sufficient period of time (temperature and pressure are not significant except to the extent required to have water present) to effect certain changes in surface morphology of the solid particles. Normally, hydration of the MgO may be carried out simply by mixing the particulate MgO with ample water and allowing the mixture to stand at room temperature, e.g., 20° C., for a sufficient period of time, e.g., 15 or more hours.

However, MgO may be hydrated "in situ" (although the benefits of the invention may not immediately accrue) in a process system where water is present in sufficient amount simply by adding particulate MgO to the water-containing mixture, especially a system operated on a continuous basis where the catalyst is reused or recycled a number of times. Hydration of the MgO produces "hydrated" MgO solids which are shown by scanning electron microscopy to be characterized by the presence of platelets and ridges on the surfaces thereof due to the action of water, as compared to normal or "unhydrated" MgO particles which possess a generally smooth amorphous surface. Further, X-ray powder diffraction analysis indicates "hydrated" MgO to possess some $Mg(OH)_2$ character, i.e., such analysis indicates the presence of hydroxyl groups at or near the surface of the particles. Additionally, IR analysis (KBr method) reveals unique absorbance bands for some samples of "hydrated" MgO prepared according to the invention, e.g., at (sh) 3702 $cm^{-1}$ and (br) 3651 $cm^{-1}$. These phenomena find support in the literature; Anderson, et al, *Trans. Faraday, J. Chem. Soc.*, (1965) 61, 2754, suggest that similar IR bands in "hydrated" MgO also indicate the presence of surface hydroxyl groups. As will be recognized by those skilled in the art, hydration of MgO particles causes some expansion and surface area modification of the particles, although this may vary with the length of the hydration treatment. Average particle size of the MgO employed in the invention (before hydration) may vary considerably, with suitable particle sizes for the MgO ranging from about 0.02 in. to about 0.5 in., preferably from about 0.05 in. to about 0.1 in. Surface areas of the MgO (before hydration) may also vary considerably, but may preferably range from about 0.1 square meters per gram to about 2.0 square meters per gram, most preferably from about 0.5 square meters per gram to about 1.0 square meters per gram. For best results, while the MgO to be hydrated need not be absolutely "pure", better grade MgO, preferably C.P. grade, is preferred.

According to the invention, the hydrated MgO is supplied in a catalytic amount. While even a minimal amount of the hydrated MgO will have some effect, the hydrated MgO normally will be supplied in a molar ratio at least 0.75, preferably 0.75 to 5.0, most preferably 0.75 to 2.0, with respect to the total amount of aldehyde present.

If the hydrated MgO is supplied to the reaction or reaction zone as an aqueous slurry, sufficient water will be employed, of course, to slurry the catalyst. Preferably, the ratio of hydrated MgO to water in a slurry, on a weight basis, will range from 1:2 to 1:20, most preferably from 1:5 to 1:10. Unless otherwise indicated herein or inconsistent with the obvious intended meaning of the text, all ratios or percentages of components stated herein are by weight, based on the total weight of the mixture including the component or components. Other non-interfering catalytic agents may be present.

The combining or contacting of the aldehyde or aldehydes and hydrated MgO is carried out under reaction conditions, i.e., those conditions of temperature, pressure, length of contact time, etc., which enable or allow the reaction to proceed. Included in such conditions are those required to supply or to maintain the aldehyde reactant(s) in the liquid phase, i. e., temperature, pressure, so that intimate contact with the hydrated MgO (and with each other in the case of cross condensation) is realized. In general, it is a great advantage of the invention that reaction conditions for the aldol condensation reaction, in the presence of the hydrated MgO, generally comprise mild temperatures and pressures. Suitable temperatures, for example, may range from 0° C. to 200° C., preferably from 20° C. to 70° C. Pressures may be varied considerably, and may range from 1 atmosphere to 20 atmospheres, preferably 1 atmosphere to 5 atmospheres. For a batch reaction, total reaction times, i.e., the time to completion or substantial completion of the condensation reaction, will vary considerably, but in general will range from 2 hours to 24 hours, preferably from 4 hours to 8 hours. In the case of a continuous process, with continuous feed to a reaction zone and continuous withdrawal of product containing mixture, average contact time may range from about 4 hours to 48 hours, preferably from about 8 hours to about 16 hours, contact time herein being understood as the liquid volume in the reactor divided by the volumetric flow rate of the liquid. In the case of condensation of n-butyraldehyde, reaction temperatures will preferably range from 0° C. to 200° C., most preferably 20° C. to 80° C., while in the cross condensation of isobutyraldehyde with formaldehyde, temperatures may range from 0° C. to 100° C., preferably 20° C. to 70° C. Pressures for these reactions may range from about 1 atmosphere to 10 atmosphere, preferably 1 atmosphere to 3.0 atmospheres, and average contact times (continuous system) may range from 4 hours to 48 hours, preferably 2 hours to 8 hours.

As indicated, the reaction may be carried out on a batch or continuous basis, but the invention is admirably suited to a continuous reaction process. In this latter preferred case, the reactant composition(s) and hydrated MgO (preferably as an aqueous slurry), are introduced, on a continuous basis, into a reaction zone maintained under the appropriate reaction conditions, the composition(s)-hydrated MgO slurry mixture, with forming reaction products, passing through and eventually being removed from the reaction zone. The degree of completion of the reaction(s) is dependent on the conditions above-mentioned, the resultant reaction product mixture being removed at an outlet of the reaction zone. The hydrated MgO may be easily separated, e.g., by centrifuging, and recycled to the reaction zone.

It is a another advantage of the invention, because alkali metal hydroxides are not employed in the reaction system, that the condensation reaction mixture may be treated, at a given degree of completion, in a desired manner, to derive a particular product. For example, if n-butyraldehyde is condensed according to the invention to form (by dehydration) 2-ethyl-2-hexenal in the reaction mixture, the crude reaction mixture containing this product may be hydrogenated directly in the reaction zone under appropriate reaction conditions known to those skilled in the art to form 2-ethylhexanol therein. Similarly, if isobutyraldehyde and formaldehyde are condensed to form hydroxypivaldehyde, the hydroxypivaldehyde may be hydrogenated directly in the reaction mixture to form neopentyl glycol. In each of these cases, the reaction mixtures may be removed from the reaction zone, and treated as desired, e. g., hydrogenation, or desired components may be separated by known techniques and then treated.

The particular techniques employed to treat the aldol formed or the unsaturated aldehyde derived by dehydration of said aldol, either in the reaction product mixture, or after separation therefrom, per se form no part of the invention, and standard procedures may be employed. In general, conditions and procedures, such as temperatures, pressures, flow rates, etc., for the hydrogenation of aldehydes or aldehyde-containing mixtures are well known or readily ascertained, e.g., as described in *Heterogeneous Catalysis*

*For The Synthetic Chemist*, copyright 1996 by Robert L. Augustine, Marcel-Dekker, Inc. (1995), pp. 439 to 457, and may be adapted or adjusted to the particular composition or mixture by those skilled in the art. If the reaction product mixture or a component thereof is to be hydrogenated, catalytic amounts of any suitable hydrogenation catalyst or catalysts will be employed. Suitable catalysts include, but are not limited to, metals and compounds of cobalt, nickel, palladium, platinum, rhodium, molybdenum, mixtures thereof, and the like. Other catalysts may comprise NiMo, NiCo, CuCr, CoMo, or CoNiMo combinations, in various proportions, and mixtures thereof.

The following experiments illustrate the practice of the invention.

I.

Hydrated MgO may be prepared in the following manner. Fused MgO crystals (c.p. grade, Strem Chemical Co.) were weighed (8.0 g., 0.40 mol) in a 250 ml beaker. Two and one-half gram-equivalents of water (20 g.) were added to the beaker, and the white MgO slurry mixture formed was stirred in air at room temperature for seventy-two hours. Scanning electron microscope analysis of the MgO after this treatment indicated changes in surface morphology, and further that crystal growth occurred during the hydration process.

II.

The following series of experiments illustrate the preparation of hydroxypivaldehyde utilizing hydrated MgO. In each experiment a slurry mixture comprising hydrated MgO in water was placed in either a round bottom flask or a 300 ml autoclave, depending on the pressure to be employed, each vessel being equipped with internal stirrer and thermocouple. Under nitrogen atmosphere, isobutyraldehyde and formalin solution (18.0 g of 37% aqueous formaldehyde; 6.7 g formaldehyde, 0.22 mol) were added to the flask or to the autoclave. The flask experiments were conducted at atmospheric pressure, while the autoclave experiments were carried out under an initial pressure of 750 psig. Temperatures were 55° C. or 65° C. in the flask runs, and 75° C. or 85° C. in the autoclave runs. Total reaction times (batch run) were varied from 270 minutes to 340 minutes in the flask experiments, while the autoclave experiments ran for 150 minutes. The conditions and results of the experiments are shown in Table 1, wherein isobutyraldehyde is designated as IHBU, and hydroxypivaldehyde is represented as HOHPV.

TABLE 1

| Concentration, Molar Equivalents | | | | Products (Mol. %) | | | Time |
|---|---|---|---|---|---|---|---|
| IHBU | CH$_2$O | MgO | T °C. | HOHPV | C$_9$ | C$_{10}$ | (Min.) |
| (flask, atmospheric pressure) | | | | | | | |
| 3 | 1 | 1 | 65 | 94.5 | 4.1 | 1.4 | 340 |
| 3 | 1 | 2 | 65 | 95.2 | 4.4 | 0.4 | 225 |
| 3 | 1 | 3 | 65 | 91 | 6.3 | 2.7 | 210 |
| 3 | 1 | 3 | 55 | 93.4 | 4.2 | 2.4 | 330 |
| 5 | 1 | 1 | 65 | 94.9 | 4.5 | 0.6 | 300 |
| 10 | 1 | 1 | 65 | 97 | 3 | 0 | 270 |
| (high pressure, 750 psig) | | | | | | | |
| 3 | 1 | 2 | 75 | 95 | 4.8 | 0.2 | 150 |
| 3 | 1 | 2 | 85 | 89 | 8.8 | 2.2 | 150 |

III.

A slurry mixture comprising 16.0 g (0.20) mol of hydrated MgO in 40 ml of water was placed in a 300 ml autoclave equipped with an internal stirrer, thermocouple, and dip tube. Isobutyraldehyde (50.0 g, 0.60 mol) and formalin solution (18.0 g of 37% aqueous formaldehyde; 6.7 g formaldehyde, 0.22 mol) of CH$_2$O were added to the catalyst slurry mixture under nitrogen atmosphere. The autoclave was pressured to an initial nitrogen pressure of 750 psig. The mixture in the autoclave was stirred and heated to a temperature of 75° C. Determination of products in the ongoing reaction was made by gas chromatography analysis and was corroborated with authentic samples and GC\ms analysis. The endpoint for the reaction was taken as a level <100 ppm of CH$_2$O in 150 minutes. When the reaction was determined to be complete, the autoclave was opened and 10 to 11 grams of Raney Ni were added to the reaction mixture. The autoclave was then resealed, repressured with hydrogen to 450 psig of H$_2$, and heated up to an internal temperature of 75° C. As head pressure dropped because of H$_2$ consumption, the autoclave was occasionally recharged with H$_2$ to maintain H$_2$ content and a pressure between 350 to 500 psig. The reaction was considered complete when H$_2$ uptake ceased. The autoclave was then cooled and depressurized, and the solids were separated from the liquid mixture. The liquid mixture was then distilled to remove volatile liquids, leaving 20.0 grams of an off-white solid residue. The solid residue was evaluated by gas chromatography, and was determined to be neopentyl glycol (NPG) having 94% (wt) purity.

IV

A slurry mixture comprising 2.0 g (0.05 mol) MgO in 10 ml of water was allowed to soak for 48 hours, and excess water was then removed therefrom by heating the mixture in an oven at 100° C. for 24 hours. After this water removal, the remaining solid was placed in a 3-neck 250 ml roundbottom flask fitted with a glass stopper or thermometer adapter, magnet spin bar, and gas inlet adapter with serum end cap. Formalin solution (18.0 g of 33.6% w/w ; 6.0 g, (0.20 mol) of CH$_2$O and 97% 2-nitropropane (35.6 g, 0.40 mol) were added to the catalyst mixture under nitrogen atmosphere. The reaction vessel was attached to a glycol cooled condenser with fitted gas inlet adapter. The mixture was stirred vigorously and brought to reflux temperature (100° C.). The determination of products in the ongoing reaction was made by gas chromatography and GC\ms analysis. The endpoint for the reaction was <100 ppm level of CH$_2$O in 180 minutes. Selectivity for 2-methyl-2-nitro-1-propanol was 100%. This nitroalcohol can be reduced to 2-amino-2-methyl-1-propanol with 100% selectivity by using 5% Pd/C. and H$_2$.

While the invention has been illustrated with particular apparatus, those skilled in the art will appreciate that other equivalent or analogous apparatus may be employed. The term "zone," as employed in the specification and claims, includes, where suitable, the use of segmented equipment operated in series, or the division of one unit into multiple units because of size constraints, etc.

What is claimed is:

1. A process for the condensation of an aldehyde comprising contacting aldehyde containing an α hydrogen atom and having the formula R$_1$CHO, wherein R$_1$ is selected from alkyl having one to twelve carbon atoms, and aralkyl having one to fourteen carbon atoms, with a catalytic amount of hydrated MgO under reaction conditions to form reaction product mixture comprising an aldol of said aldehyde, the unsaturated aldehyde derived by dehydration of said aldol, or mixtures thereof.

2. The process of claim 1 wherein the molar ratio of hydrated MgO to total aldehyde present is at least 0.75.

3. The process of claim 1 wherein aldol is recovered from reaction product mixture.

4. The process of claim 1 wherein the unsaturated aldehyde derived by dehydration of said aldol is recovered from reaction product mixture.

5. The process of claim 1 wherein hydrated MgO is recovered from the reaction product mixture.

6. The process of claim 1 wherein the hydrated MgO is supplied as an aqueous slurry.

7. The process of claim 2 wherein reaction product mixture is contacted with hydrogen in the presence of a catalytic amount of hydrogenation catalyst under conditions to hydrogenate an aldol of said aldehyde or the unsaturated aldehyde derived by dehydration of said aldol.

8. The process of claim 4 wherein said unsaturated aldehyde recovered from reaction product mixture is contacted with hydrogen in the presence of a catalytic amount of hydrogenation catalyst under conditions to hydrogenate said unsaturated aldehyde.

9. A process for the condensation of an aldehyde comprising contacting in a reaction zone an aldehyde containing an α hydrogen atom and having the formula $R_1CHO$, wherein $R_1$ is selected from alkyl having one to twelve carbon atoms, and aralkyl having one to fourteen carbon atoms, with an aqueous slurry containing a catalytic amount of hydrated MgO, under reaction conditions, to form reaction product mixture comprising an aldol of said aldehyde, the unsaturated aldehyde derived by dehydration of said aldol, or mixtures thereof, and hydrated MgO; and removing reaction product mixture from the reaction zone and separating hydrated MgO from the reaction product mixture removed from the reaction zone.

10. The process of claim 9 wherein hydrated MgO separated from the reaction product mixture removed from the reaction zone is supplied to the reaction zone for contact with the aldehyde.

11. A process comprising contacting in a reaction zone an aldehyde containing an α hydrogen atom and having the formula $R_1CHO$, wherein $R_1$ is selected from alkyl having one to twelve carbon atoms, and aralkyl having one to fourteen carbon atoms, with an aqueous slurry containing a catalytic amount of hydrated MgO, under reaction conditions, to form reaction product mixture comprising an aldol of said aldehyde, the unsaturated aldehyde derived by dehydration of said aldol, or mixtures thereof, and hydrated MgO; contacting reaction product mixture in the reaction zone with hydrogen in the presence of a catalytic amount of hydrogenation catalyst under conditions to hydrogenate an aldol of said aldehyde or the unsaturated aldehyde derived by dehydration of said aldol, forming hydrogenated product admixture;

and removing hydrogenated product admixture from the reaction zone and separating hydrated MgO from the hydrogenated product admixture removed from the reaction zone.

12. A process comprising contacting in a reaction zone an aldehyde containing an α hydrogen atom and having the formula $R_1CHO$, wherein $R_1$ is selected from alkyl having one to twelve carbon atoms, and aralkyl having one to fourteen carbon atoms, with an aqueous slurry containing a catalytic amount of hydrated MgO, under reaction conditions, to form reaction product mixture comprising an aldol of said aldehyde, the unsaturated aldehyde derived by dehydration of said aldol, or mixtures thereof, and hydrated MgO; removing reaction product mixture from the reaction zone and contacting reaction product mixture removed from the reaction zone with hydrogen in the presence of a catalytic amount of hydrogenation catalyst under conditions to hydrogenate an aldol of said aldehyde or the unsaturated aldehyde derived by dehydration of said aldol, forming a hydrogenated product mixture;

and separating hydrated MgO from the hydrogenated product mixture.

13. An aldehyde condensation process comprising combining a first aldehyde selected from aldehydes containing an α hydrogen atom and having the formula $R_1CHO$, wherein $R_1$ is selected from alkyl having one to twelve carbon atoms, and aralkyl having one to fourteen carbon atoms, with a second different aldehyde selected from aldehydes having the formula $R_2CHO$, wherein $R_2$ is selected from H, alkyl having one to twelve carbon atoms, and aralkyl having one to fourteen carbon atoms, and with a catalytic amount of hydrated MgO under reaction conditions to form reaction product mixture comprising an aldol of said aldehydes, the unsaturated aldehyde derived by dehydration of said aldol, and mixtures thereof.

14. The process of claim 13 wherein the molar ratio of hydrated MgO to total aldehyde present is at least 0.75.

15. The process of claim 13 wherein aldol is recovered from reaction product mixture.

16. The process of claim 13 wherein the unsaturated aldehyde derived by dehydration of said aldol is recovered from reaction product mixture.

17. The process of claim 13 wherein hydrated MgO is recovered from reaction product mixture.

18. The process of claim 13 wherein the hydrated MgO is supplied as an aqueous slurry.

19. The process of claim 14 wherein reaction product mixture is contacted with hydrogen in the presence of a catalytic amount of hydrogenation catalyst under conditions to hydrogenate an aldol of said aldehyde or the unsaturated aldehyde derived by dehydration of said aldol.

20. The process of claim 16 wherein said unsaturated aldehyde recovered from reaction product mixture is contacted with hydrogen in the presence of a catalytic amount of hydrogenation catalyst under conditions to hydrogenate said unsaturated aldehyde.

21. A process comprising contacting n-butyraldehyde in a reaction zone with a catalytic amount of hydrated MgO under reaction conditions to form reaction product mixture comprising the aldol of n-butyraldehyde, 2-ethyl-2-hexenal, or mixtures thereof.

22. The process of claim 21 wherein the molar ratio of hydrated MgO to total aldehyde present is at least 0.75.

23. The process of claim 22 wherein the hydrated MgO is supplied as an aqueous slurry.

24. The process of claim 23 wherein reaction product mixture is contacted with hydrogen in the presence of a catalytic amount of hydrogenation catalyst under conditions to hydrogenate 2-ethyl-2-hexenal in said reaction product mixture to 2-ethyl-2-hexanol.

25. The process of claim 23 wherein 2-ethyl-2-hexenal is recovered from reaction product mixture and is contacted with hydrogen in the presence of a catalytic amount of hydrogenation catalyst under conditions to hydrogenate said 2-ethyl-2-hexanol.

26. A process comprising combining isobutyraldehyde with formaldehyde and a catalytic amount of hydrated MgO under reaction conditions to form reaction product mixture comprising hydroxypivaldehyde.

27. The process of claim 26 wherein the molar ratio of hydrated MgO to total aldehyde present is at least 0.75.

28. The process of claim 27 wherein the hydrated MgO is supplied as an aqueous slurry.

29. The process of claim 27 wherein reaction product mixture is contacted with hydrogen in the presence of a catalytic amount of hydrogenation catalyst under conditions to hydrogenate hydroxypivaldehyde in the reaction product mixture to neopentyl glycol.

30. The process of claim 27 wherein hydroxypivaldehyde is recovered from reaction product mixture and is contacted with hydrogen in the presence of a catalytic amount of hydrogenation catalyst under conditions to hydrogenate said hydroxypivaldehyde.

31. The process of claim 18 wherein reaction product mixture is contacted with hydrogen in the presence of a catalytic amount of hydrogenation catalyst under conditions to hydrogenate an aldol of said aldehyde or the unsaturated aldehyde derived by dehydration of said aldol, forming hydrogenated product admixture; the hydrogenated product admixture is removed from the reaction zone, and hydrated MgO is separated from the hydrogenated product admixture removed from the reaction zone.

32. The process of claim 18 wherein reaction product mixture is removed from the reaction zone, removed reaction product mixture is contacted with hydrogen in the presence of a catalytic amount of hydrogenation catalyst under conditions to hydrogenate an aldol of said aldehyde or the unsaturated aldehyde derived by dehydration of said aldol, forming hydrogenated product admixture; and hydrated MgO is separated from the hydrogenated product admixture.

* * * * *